US010653724B2

(12) United States Patent
Aizman

(10) Patent No.: US 10,653,724 B2
(45) Date of Patent: *May 19, 2020

(54) EXTRACELLULAR MATRIX FROM PLURIPOTENT CELLS

(71) Applicant: SanBio, Inc., Mountain View, CA (US)

(72) Inventor: Irina Aizman, Mountain View, CA (US)

(73) Assignee: SanBio, Inc., Mountain View, CA (US)

( * ) Notice: Subject to any disclaimer, the term of this patent is extended or adjusted under 35 U.S.C. 154(b) by 104 days.

This patent is subject to a terminal disclaimer.

(21) Appl. No.: 15/870,701

(22) Filed: Jan. 12, 2018

(65) Prior Publication Data

US 2018/0140636 A1    May 24, 2018

Related U.S. Application Data

(62) Division of application No. 12/734,855, filed as application No. PCT/US2008/013297 on Dec. 3, 2008.

(60) Provisional application No. 61/005,125, filed on Dec. 3, 2007, provisional application No. 61/197,641, filed on Oct. 29, 2008.

(51) Int. Cl.
    *A61K 35/28* (2015.01)
    *C12N 5/0775* (2010.01)
    *C12N 5/0793* (2010.01)
    *C12N 5/079* (2010.01)
    *A61K 35/12* (2015.01)

(52) U.S. Cl.
    CPC ............ *A61K 35/28* (2013.01); *C12N 5/0619* (2013.01); *C12N 5/0622* (2013.01); *C12N 5/0663* (2013.01); *A61K 35/12* (2013.01); *A61K 2035/124* (2013.01); *C12N 2501/42* (2013.01); *C12N 2510/00* (2013.01); *C12N 2533/90* (2013.01)

(58) Field of Classification Search
    None
    See application file for complete search history.

(56) References Cited

U.S. PATENT DOCUMENTS

| | | |
|---|---|---|
| 4,829,000 A | 5/1989 | Kleinman et al. |
| 5,830,708 A | 11/1998 | Naughton |
| 8,945,919 B2 | 2/2015 | Mori et al. |
| 2003/0003090 A1 | 1/2003 | Prockop et al. |
| 2006/0166362 A1 | 11/2006 | Dezawa et al. |
| 2006/0251624 A1 | 11/2006 | Dezawa |
| 2007/0128722 A1 | 6/2007 | Lin et al. |
| 2010/0310529 A1 | 12/2010 | Aizman |
| 2014/0363408 A1 | 12/2014 | Aizman |
| 2018/0221414 A1 | 8/2018 | Aizman |

FOREIGN PATENT DOCUMENTS

| | | |
|---|---|---|
| WO | WO 1996/039101 | 12/1996 |
| WO | WO 2009/073178 | 6/2009 |

OTHER PUBLICATIONS

Hartmann, Christopher; et al; "The impact of glia-derived extracellular matrices on the barrier function of cerebral endothelial cells: An in vitro study" Experimental Cell Research, 313, 1318-1325, 2007 (Year: 2007).*
Oh, Luke YS; Yong, Voon Wee; "Astrocytes Promote Process Outgrowth by Adult Human Oligodendrocytes In Vitro Through Interaction Between bFGF and Astrocyte Extracellular Matrix" Glia, 17, 237-253, 1996 (Year: 1996).*
Aizman et al., "Extracellular Matrix Produced by Bone Marrow Stromal Cells and by Their Derivatne, SB623 Cells, Supports Neural Cell Growth," J Neurosci. Res. 87(14):3198-3206 (2009).
Alovskaya, A. et al., "Fibronectin, Collagen, Fibrin-Components of Extracellular Matrix for Nerve regeneration," Topics in Tissue Engineering, vol. 3, 2007.
Ard et al., "Comparison of TIIE SCHW Ann Cell Surf Ace and SCHW Ann Cell Extracellular Matrix as Promoters of Neurite Growtii," J Neurocytol. 16(4): 539-556 (1987).
Bai et al., "Human Mesenchymal Stem Cells Signals Regulate Neural Stem Cells Signals Regulate Neural Stem Cell Fate," Neurochem. Res. 32(2):353-362 (2007).
Borland et at., "Production of Components of Extracellular Matrix by Cultured Rat Sertoli Cells," Biol Reprod 35: 997-1008 (1986).
Chen et al., "Extracellular Matrix Made by Bone Marrow Cells Facilitates Expansion of Marrow-Derned Mesenchymal Progenitor Cells and Prevents Their Differentiation Into Osteoblasts," J. Bone Miner Res. 22(12):1943-1956 (2007).
Darnell, J.E. et al., "Molecular Cell Biology," Second Edition, Scientific American Books, New York, NY, p. 904 (1990).
Datta Neha et al., "In vitro generated extracellular matrix and fluid shear stress synergistically enhance 3D osteoblastic differentiation," Proceedings of the National Academy of Sciences of the United States of America, vol. 103, No. 8, pp. 2488-2493 (Feb. 2006).
De Curtis et al., "Neuronal Interactions With the Extracellular Matrix," Curr Opin Cell Biol., 3(5):824-831 (1991).
Dezawa, et al., "Specific Induction of Neuronal Cells From Bone Marrow Stromal Cells and Application for Autologous Transplantation," J Clin Invest 113(12):1701-1710 (2004).
El-Amin et al., "Extracellular matrix production by human osteoblasts cultures on biodegradable polymers for tissue engineering," Biomaterials, vol. 23, pp. 1213-1221 (2003).
Ellisen, et al., "Tan-I, the Human Homolog of the *Drosophila* Notch Gene, is Broken by Chromosomal Translocations in T Lymphoblastic Neoplasms," Cell 66:649-661 (1991).

(Continued)

*Primary Examiner* — David W Berke-Schlessel
(74) *Attorney, Agent, or Firm* — Levine Bagade Han LLP

(57) ABSTRACT

Isolated extracellular matrix from marrow adherent stromal cells and their descendents, which stimulates the growth and survival of a number of different neural cell types, is provided, along with methods for preparation and uses.

15 Claims, 5 Drawing Sheets

(56) References Cited

Fawcett, D.W., "Bloom and Fawcett: A Textbook of Histology," Eleventh Edition, W.B. Saunders Co., Philadelphia, p. 151 (1986).
Gu et al., "A Highly Specific Inhibitor of Matrix Metalloproteinase-9 Rescues Laminin From Proteolysis and Neurons From Apoptosis in Transient Focal Cerebral Isochemia," Journal of Neuroscience 25(27):6401-6408 (2005).
Harvey et al., "Proteomic Analysis of the Extracellular Matrix Produced by Mesenchymal Stromal Cells: Implications for Cell Therapy Mechanism," PLOS One, 8(11):e79283, Nov. 2013.
Kromer et al., "Transplants of Schwann Cell Cultures Promote Axonal Regeneration in the Adult Mamallian Brain," PNAS USA 82(18):6330 (1985).
McCarthy, James B. et al, "Migration by Haptotaxis of a Schwann Cell Tumor Line to the Basement Membrane Glycoprotein Laminin," The Journal of Cell Biology, 97:772-777, 1983.
Needham et al., "Selective Growth of Rat SCHW Ann Cells in Neuron- and Serumfree Primary Culture," Journal of Neuroscience, 7(1):1-9 (1987).

Novak, Ulrike et al., "Extracellular matrix and the brain: components and function," Journal of Clinical Neuroscience, 7:280-290, 2000.
Pfefferkorn et al., "Closure of the Blood-Brain Barrier by Matrix Metalloproteinase Inhibition Reduces rtPA-Mediated Mortality in Cerebral Ischemia With Delayed Reperfusion," Stroke 34(8):2025-2030 (2003).
Qian et al., "Improving the Expansion and Neuronal Differentiation of Mesenchymal Stem Cells Through Culture Surface Modification," Biomaterials 25:1331-1337 (2004).
Sadovnikov A et al., "Induction of Hematopoietic Microenvironment by the Extracellular Matrix From Long-Term Bone Marrow Cul Tures," Ann Hematol., 62(5):160-164 (1991).
Tohill, Mel, et al., "Stem-cell plasticity and therapy for injuries of the peripheral nervous system," Biotechnology and Applied Biochmeistry, 40:17-24, 2004.
Yang et al., "Effects of Bone Marrow Stromal Cell-Conditioned Medium on Primary Cultures of Peripheral Nerve Tissues and Cells," Neurochemical Research, 34(9):1685-1694 (2009).
Yasuda, Hiroshi et al., "Effect of biodegradable fibrin scaffold on survival, migration, and differentiation of transplanted bone marrow stromal cells after cortical injuriy in rats Laboratory investigation," J. Neurosurg, 112(2):336-344, Feb. 1, 2010.
Zhang, Jian et al., "Enhancement of rat sciatic nerve regeneration by fibronectin and laminin through a silicone chamber," Journal of Reconstructive Microsurgery, 19(7):467-472, Oct. 1, 2003.
Zhou, F. C. et al., "Laminin facilitates and guides fiber growth of transplanted neurons in adult brain," Journal of Chemical Neuroanatomy, 1(3):133-146, May 1, 2988.

* cited by examiner

US 10,653,724 B2

EXTRACELLULAR MATRIX FROM PLURIPOTENT CELLS

CROSS-REFERENCE TO RELATED APPLICATIONS

This application is a divisional of U.S. patent application Ser. No. 12/734,855 filed on Aug. 23, 2010, which is a national phase under 35 U.S.C. § 371 of International Patent Application No. PCT/US2008/013297 filed Dec. 3, 2008, which claims the benefit of U.S. Provisional Application Nos. 61/005,125 filed Dec. 3, 2007 and 61/197,641 filed Oct. 29, 2008, the contents of which are incorporated herein by reference in their entirety.

BACKGROUND OF THE INVENTION

The present disclosure is in the fields of neural growth and development and neural regeneration.

Stem cell-based therapy is a novel approach to the treatment of neurological disorders. Such therapies involve the transplantation of neural stem cells, neural precursor cells, embryonic stem cells or adult stem cells, sometimes modified or pre-differentiated, into sites of neuronal injury or degeneration. Although precise mechanisms of action of stem cells transplanted to sites of injury are not known, the current view is that the beneficial effect of grafted stem cells on injured neural tissue derives either from replacement of endogenous cells, and/or secretion of neurotrophic factors, by the transplanted stem cells.

One concern associated with the use of embryonic stem cells for cell therapy is the possibility of oncogenic transformation of the grafted cells.

Another, universal problem associated with transplantation of stem cells into the brain, is the limited survival of grafted cells. For example, adult stem cells of mesenchymal origin (e.g., bone marrow, adipose tissue) have provided some promise for treatment of indications such as stroke, Parkinson's disease, and brain or spinal cord trauma; due to ease of their isolation, low immunogenicity, and low tendency toward oncogenic transformation. However, their typical engraftment rates are very low.

The poor long-term survival of bone marrow stem cells (BMSC) injected into the brain may be explained in part by their inability to adapt to microenvironments in the brain, which is atypical for mesenchymal cells, and may be unfavorable for their long-term growth and differentiation. Inflammation at a site of injury (due either to the initial neural trauma or to the transplantation procedure) could also be detrimental to the survival of engrafted cells.

The degree to which long-term survival of engrafted cells is important for repair of neural degeneration is unknown. However, the fact that beneficial effects are observed in cases in which survival of transplanted stem cells is very low implies the possible participation, in the repair process, of cellular products produced soon after transplantation, when injected cells are still alive. If this is the case, low survival of transplanted stem cells could result in decreased production of extracellular products that stimulate neural regeneration.

Because of the risk of oncogenic transformation associated with the use of embryonic stem cells, and the poor survival of adult stem cells, methods for treatment of neural disorders that take advantages of the unique properties of stem cells, and/or utilized unique extracellular products elaborated by stem cells, would have advantages over the use of stem cells themselves.

BRIEF SUMMARY OF THE INVENTION

The present disclosure provides isolated extracellular matrix produced by various types of pluripotent cells, including marrow adherent stromal cells (also known as mesenchymal stem cells), differentiation-restricted descendents of marrow adherent stromal cells and neural progenitor cells.

Also provided are methods for the production of the aforementioned isolated extracellular matrices, and methods for the use of the aforementioned isolated extracellular matrices in the treatment of neural injury, neural trauma, neural disorders and neural degeneration.

Accordingly, the following embodiments are provided.

A method for producing an isolated extracellular matrix, the method comprising culturing MASCs on a culture surface and isolating the extracellular matrix deposited on the culture surface.

A method for producing an isolated extracellular matrix, the method comprising culturing differentiation-restricted descendents of MASCs (DRCs) on a culture surface and isolating the extracellular matrix deposited on the culture surface.

A method for producing an isolated extracellular matrix, the method comprising culturing differentiation-restricted descendents of MASCs (DRCs) on a culture surface, wherein the DRCs result from transfection of a culture of MASCs with a nucleic acid comprising sequences encoding a notch intracellular domain.

An isolated extracellular matrix produced by a marrow adherent stromal cell (MASC).

An isolated extracellular matrix produced by a differentiation-restricted descendant of a marrow adherent stromal cell (DRC).

A method for stimulating the growth of neurons, the method comprising culturing MASCs on a culture surface; removing the MASCs from the culture surface; transferring a population of cells onto the culture surface; and incubating the cells on the culture surface.

A method for stimulating the growth of astrocytes, the method comprising culturing MASCs on a culture surface; removing the MASCs from the culture surface; transferring a population of cells onto the culture surface; and incubating the cells on the culture surface.

A method for stimulating the growth of oligodendrocytes, the method comprising culturing MASCs on a culture surface; removing the MASCs from the culture surface; transferring a population of cells onto the culture surface; and incubating the cells on the culture surface.

A method for stimulating the growth of neurons, the method comprising culturing differentiation-restricted descendents of MASCs (DRCs) on a culture surface; removing the DRCs from the culture surface; transferring a population of cells onto the culture surface; and incubating the cells on the culture surface.

A method for stimulating the growth of astrocytes, the method comprising culturing differentiation-restricted descendents of MASCs (DRCs) on a culture surface; removing the DRCs from the culture surface; transferring a population of cells onto the culture surface; and incubating the cells on the culture surface.

A method for stimulating the growth of oligodendrocytes, the method comprising culturing differentiation-restricted descendents of MASCs (DRCs) on a culture surface; removing the DRCs from the culture surface; transferring a population of cells onto the culture surface; and incubating the cells on the culture surface.

A method for treating neural degeneration or disorder in a subject, the method comprising transplanting an isolated extracellular matrix to a site in a subject.

A method for treating neural degeneration or disorder in a subject, the method comprising transplanting one or more extracellular matrix components to a site in a subject.

A method for treating neural degeneration or disorder in a subject, the method comprising transplanting an isolated extracellular matrix to a site in a subject, wherein the extracellular matrix is produced by a culture of MASCs.

A method for treating neural degeneration or disorder in a subject, the method comprising transplanting an isolated extracellular matrix to a site in a subject, wherein the extracellular matrix is produced by a culture of differentiation-restricted descendents of MASCs.

A method for treating neural degeneration or disorder in a subject, the method comprising co-transplanting MASCs and an isolated extracellular matrix to a site in a subject.

A method for treating neural degeneration or disorder in a subject, the method comprising co-transplanting MASCS and one or more extracellular matrix components to a site in a subject.

A method for treating neural degeneration or disorder in a subject, the method comprising co-transplanting MASCs and an isolated extracellular matrix to a site in a subject, wherein the extracellular matrix is produced by a culture of MASCs.

A method for treating neural degeneration or disorder in a subject, the method comprising co-transplanting MASCs and an isolated extracellular matrix to a site in a subject, wherein the extracellular matrix is produced by a culture of differentiation-restricted descendents of MASCs.

A method for treating neural degeneration or disorder in a subject, the method comprising co-transplanting DRCs and an isolated extracellular matrix to a site in a subject.

A method for treating neural degeneration or disorder in a subject, the method comprising co-transplanting DRCs and one or more extracellular matrix components to a site in a subject.

A method for treating neural degeneration or disorder in a subject, the method comprising co-transplanting DRCs and an isolated extracellular matrix to a site in a subject, wherein the extracellular matrix is produced by a culture of MASCs.

A method for treating neural degeneration or disorder in a subject, the method comprising co-transplanting DRCs and an isolated extracellular matrix to a site in a subject, wherein the extracellular matrix is produced by a culture of differentiation-restricted descendents of MASCs (DRCs).

DETAILED DESCRIPTION OF THE INVENTION

Figure 1:
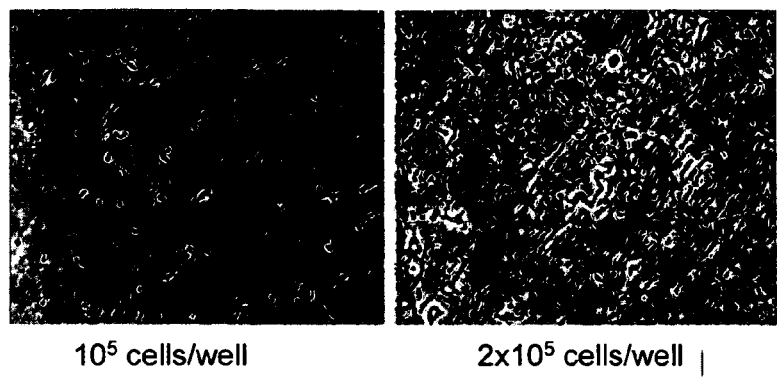
FIG. 1 shows micrographs (400×) of extracellular matrix deposited by two concentrations of MASCs.

The terms "bone marrow stromal cells," "marrow adherent stromal cells," "marrow adherent stem cells," "marrow stem cells," "mesenchymal stem cells" and "MASCs" refer to mitotic, pluripotent cells, obtained from bone marrow that, in the course of normal development, are capable of giving rise to a number of differentiated cell types such as, for example, osteocytes, and cells normally found in connective tissue including, but not limited to, chondrocytes and adipocytes. MASCs can be human cells or cells from other mammals or vertebrates.

The terms "neural precursor cell," "neuronal precursor cell," "neural progenitor cell," "neuronal progenitor cell," "NPC" and bone marrow-derived neural progenitor cell" are used interchangeably to refer to mitotic cells, descended from marrow adherent stromal cells, that have the capability to differentiate into neurons, glial cells, or their precursors. They are thus distinct from primary neuronal precursor cells, such as can be obtained from fetuses or adult tissues such as the hippocampus and the periventricular subependymal zone. NPCs can be human cells or cells from other mammals or vertebrates.

For the purposes of this disclosure, the terms "differentiation-restricted cell" and "DRC" refer to a cell, descended from a mesenchymal stem cell, whose normal lineage specification (to mesenchymal lineages such as osteocytes, chondrocytes and adipocytes) has been restricted. That is, the ability of such a cell to enter a lineage resulting in terminal differentiation into osteocytes, adipocytes and/or chondrocytes is reduced. A differentiation restricted cell may optionally acquire one or more new developmental potentials including but not limited to the ability to enter a neural lineage and differentiate into neurons and/or glial cells and the ability to enter a myogenic lineage. Thus, certain differentiation-restricted cells may also be neural precursor cells.

Marrow adherent stromal cells are easily extracted by bone marrow aspiration on an outpatient basis, and due to their highly proliferative nature they can be cultured in large amounts within a relatively short period. Moreover, a further advantage of their use as starting material for various types of cell therapy is that they allow autologous transplantation to be carried out (e.g., new muscular and/or neural tissue can be formed from cells derived from the patient's own bone marrow stem cells). The consequent lack of immunological rejection dispenses with the need for administering immunosuppressants, thus enabling safer treatment. Furthermore, since bone marrow stem cells can be obtained from a bone marrow bank, this method is also advantageous from a supply standpoint.

Marrow adherent stromal cells are obtained from bone marrow aspirates by culturing for three days in α-MEM+ 10% FBS+L-Glutamine, then aspirating away non-adherent cells. See Example 1 below for an exemplary method for extraction and expansion of marrow adherent stromal cells.

In certain embodiments, differentiation-restricted cells and/or neural precursor cells are obtained by methods comprising transfection of marrow adherent stromal cells with a polynucleotide comprising a sequence encoding a Notch intracellular domain (NICD) as described, for example, in US Patent Application Publication No. 2006-0166362 (Jul. 27, 2006), the disclosure of which is incorporated by reference, and Dezawa et al. (2004) J. Clin. Invest. 113:1701-1710. In certain of these embodiments, the Notch intracellular domain consists of amino acids 1703-2504 of the human Notch-1 protein. Ellison et al. (1991) Cell 66:649-661. In additional embodiments, differentiation-restricted cells are obtained as described in US Patent Application Publication No. 2006-0251624 (Nov. 9, 2006), the disclosure of which is incorporated by reference. Alternatively, such cells can be obtained as described in US Patent Application Publication No. 2003-0003090 (Jan. 2, 2003), the disclosure of which is incorporated by reference. Example 2 describes an exemplary method for the preparation of DRCs.

Stem cells, of both embryonic and adult provenance, have been used for the treatment of various neurological diseases and disorders by transplantation of stem cells to sites of neural injury or degeneration. Although precise mechanisms of action of stem cells in sites of injury are not known, the common view is that the beneficial effect of grafted stem cells on neural tissue result from cell replacement and/or secretion of neurotrophic factors by transplanted stem cells. However, another possible mechanism involves the synthesis and/or secretion of extracellular matrix (ECM) molecules by grafted cells. This mechanism may be especially relevant to rescue of neural tissue by adult stem cells of mesenchymal origin, since these cells make large amounts of ECM as part of their normal developmental progression into the various cells of connective tissue. ECM could serve as a source of matrix-bound growth factors, i.e. a source of chemotactic and haptotactic stimuli for neurons and glia.

The present disclosure shows that isolated extracellular matrix, produced by mesenchymal stem cells or their descendents, efficiently supports survival and growth of neurons, neurite outgrowth and growth and proliferation of glial cells. Accordingly, extracellular matrix produced by adult mesenchymal stem cells and their descendents (such as, for example, differentiation-restricted cells and neural precursor cells) can be used, instead of or in addition to, stem cell therapy and/or other types of therapy to repair injury or degeneration of neural tissue, in both the central and peripheral nervous systems. These methods are to be distinguished from conventional methods involving insertion of cell suspensions into sites of neural injury, and from the use of engineered (e.g., non-biological) materials as a scaffold or implant for grafting stem cells to repair spinal cord injuries.

The extracellular matrix produced by MASCs and their differentiation-restricted descendents can be produced in situ by MASCs or DRCs following their transplantation to a site of injury.

Alternatively, ECM derived from MASCs or DRCs can be collected and transplanted (e.g., injected as liquid or gel) into injured sites to provide a substrate for growth and/or repair of neural tissue, and possibly to provide chemotactic and/or haptotactic stimuli for neuronal outgrowth. ECM can be collected from the surface of vessels in which MASCs or DRCs are growing by lysing cells, optionally removing cell debris and optionally solubilizing the matrix. Alternatively, nascent ECM molecules, such as proteins, glycoproteins and proteoglycans can be collected (prior to their deposition and incorporation into the matrix) from spent or conditioned medium of MASC cultures, and optionally concentrated and/or purified.

Exemplary ECM components that can be used, in the disclosed embodiments, alone, in combination, or as part of an ECM include, for example, ECM remodeling enzymes, collagens, laminins, matrix metalloproteases and/or their inhibitors (e.g., tissue inhibitor of matrix metalloprotease (TIMP)), tenascins, fibulins, syndecans, perlecans, fibronectins, collagen, fibrins, heparans, decorins and biglycans. See also Alovskaya et al., "Fibronectin, Collagen, Fibrin—Components of Extracellular Matrix for Nerve Regeneration" in Topics in Tissue Engineering, Vol. 3, Eds. N. Ashammakhi, R. Reis & E. Chiellini, 2007.

In additional embodiments, isolated ECM can be co-transplanted with cells (e.g., either MASCs or DRCs), e.g., to enhance engraftment and/or prolong survival of the transplanted cells. Without wishing to be bound by theory, it is possible that transplanted ECM provides a substrate for growth of transplanted cells, leading to enhanced survival at the transplant site, and possibly facilitating migration of transplanted cells from the transplant site to one or more sites of injury.

In further embodiments, isolated ECM can be used as a coating on artificial surfaces, that can optionally be implanted and used to provide direction or support for growth of injured neural cells. Isolated ECM can also be collected as a chemically unmodified layer, or "rug," of needed size, and implanted into a site of injury using a micromanipulator.

In other embodiments, ECM can be used as coating on plates for studying neural cell behavior.

For all of the aforementioned embodiments, the concentration of cells used to elaborate an ECM can vary according to the particular embodiment. For example, in certain embodiments, MASCs or DRCs can be plated at densities of 0.25, 0.5, 1, 2, 4, 5, 8, 15, 30, 60, or $100 \times 10^3$ or more cells/cm$^2$, and cultured for 1, 2, 3, 4, 5, 7, 10, 13, 15, 17 or 20 days or more. Any value within these ranges is also contemplated.

The examples below show that the extracellular matrix (ECM) elaborated by MASCs and their descendents (e.g., DRCs) supports growth of various neural cells including neurons, astrocytes and oligodendrocytes. The efficiency of this support is dose-dependent, with respect to the number of cells used to produce the matrix. Thus, isolated ECM can be used to generate neurosupport, and to stimulate and direct the growth of various neural cells, both in vivo and in vitro.

The methods and compositions disclosed herein involve the use of art-recognized procedures in molecular biology, cell biology and cell culture. Such methods are known to those of skill in the art and have been disclosed, e.g., in Sambrook et al. "Molecular Cloning: A Laboratory Manual," Third Edition, Cold Spring Harbor Laboratory Press, 2001; Ausubel et al., "Current Protocols in Molecular Biology," John Wiley & Sons, New York, 1987 and periodic updates; R. I. Freshney "Culture of Animal Cells: A Manual of Basic Technique," Fifth Edition, Wiley, N.Y., 2005; and Kandel E R, Schwartz J H, Jessell T M, Principles of Neural Science, 4th ed. McGraw-Hill, New York, 2000.

EXAMPLES

Example 1: Preparation of Marrow Adherent Stromal Cells (MASCs)

Bone marrow aspirates, obtained from human donors, were divided into 12.5 ml aliquots in 50 ml tubes, and 12.5 ml of growth medium (10% FBS in α-MEM, supplemented with penicillin/streptomycin and 2 mM L-glutamine) was added to each tube. The contents of the tubes were mixed by inversion and the tubes were centrifuged at 200×g for 8 minutes. The upper, clear phase was discarded, the volume of the lower phase was adjusted to 25 ml with fresh growth medium, and the tubes were again mixed and centrifuged. The upper layer was again removed. The volume of the lower phase in each tube was again adjusted to 25 ml and the contents of all tubes were pooled in a 250 ml tube. After determination of cell concentration by Trypan Blue exclusion and determination of nucleated cell count, cells were plated in T225 flasks, in 40 ml per flask of growth medium at a density of $100 \times 10^6$ total nucleated cells per flask. The flasks were incubated at 37° C. for 3 days in a CO$_2$ incubator, during which time the MASCs attached to the flask.

After 3 days, unattached cells were removed by rocking the flasks and withdrawing the culture medium. Each flask was washed three times with 40 ml of α-MEM supplemented with penicillin/streptomycin; then 40 ml of pre-warmed (37° C.) growth medium was added to each flask and the cells were cultured at 37° C. in a CO$_2$ incubator. During this time, the medium was replaced with 40 ml of fresh growth medium every 3-4 days, and cells were monitored for growth of colonies and cell density.

When the cultures achieved 25-30% confluence (usually 10,000-20,000 cells per colony and within 10-14 days), the MASCs (passage M0) were harvested for further passage. MASCs were harvested from up to 10 T-225 flasks at a time. Medium was removed from the flasks and the adherent cells were rinsed with 20 ml of DPBS w/o Ca/Mg (DPBS −/−, HyClone) 2 times. Ten ml of 0.25% Trypsin/EDTA (Invitrogen, Carlsbad, Calif.) was added to each flask and flasks were incubated for approximately 5 min at room temperature. When cells had detached and the colonies had dispersed into single cells, the trypsin was inactivated by addition of 10 ml of growth medium followed by gentle mixing. The cell suspensions were withdrawn from the flasks, and pooled in 250 ml tubes. The tubes were subjected to centrifugation at 200×g for 8 minutes. The supernatants were carefully removed and the wet cell pellets were resuspended in growth medium to an estimated cell concentration of approximately $1 \times 10^6$ cells/ml. Viable cell count was determined and cells were plated in T225 flasks at a concentration of $2 \times 10^6$ cells per flask in growth medium (passage M1). Cells were grown for 3-5 days, or until 85-90% confluent, changing medium every 2 to 3 days. At 85-90% confluence, passage M1 cells were harvested by trypsinization and replated at $2 \times 10^6$ cells per T225 flask as described above, to generate passage M2 cultures. M2 cultures were fed fresh medium every three days, if necessary. When passage M2 cultures reached 85-90% confluence (usually within 3-5 days), they were either harvested for transfection to generate DRCs (Example 2 below) or frozen for future use (Example 3 below).

MASCs prepared in this fashion were positive (>95%) for CD29, CD90 and CD105, and negative (<5%) for CD31, CD34 and CD45.

Example 2: Preparation of Differentiation-Restricted Cells (DRCs)

DRCs were made either directly from MASCs harvested from passage M2 cultures, or from passage M2 MASCs that had been frozen as described in Example 3, and thawed and revived as described in Example 4.

A. Preparation of Transfection Mixture

Differentiation-restricted cells were made by transfection of passage M2 MASCs with a plasmid encoding the Notch intracellular domain. The plasmid (pCI-Notch) comprised a pCI-neo backbone (Promega, Madison, Wis.) in which sequences encoding amino acids 1703-2504 of the human Notch-1 protein, which encode the intracellular domain, were introduced into the multiple cloning site. For each flask of MASCs, 5 ml of transfection mixture, containing 40 μg of plasmid and 0.2 ml of Fugene 6® solution, was used. To make the transfection mixture, the appropriate amount of Fugene® solution (depending on the number of flasks of cells to be transfected) was added to α-MEM in a sterile 250 ml tube, using a glass pipette. The solution was mixed gently and incubated for 5 min at room temperature. The appropriate amount of plasmid DNA was then added dropwise to the Fugene®/α-MEM mixture, gently mixed, and incubated for 30 min at room temperature.

Prior to the addition of pCI-Notch DNA to the Fugene®/MEM mixture, 5 ml was removed and placed into a 15 ml tube to which was added 40 ug of pEGFP plasmid. This solution was used to transfect one flask of cells, as a control for transfection efficiency.

B. Transfection

For transfection, passage M2 MASCs were harvested by trypsinization (as described in Example 1) and plated at a density of $2.5 \times 10^6$ cells in 40 ml of growth medium per T225 flask. When the cells reached 50-70% confluence (usually within 18-24 hours) they were prepared for transfection, by replacing their growth medium with 35 ml per flask of transfection medium (α-MEM+10% FBS without penicillin/streptomycin).

Three hours after introduction of transfection medium, 5 ml of the transfection mixture (Section A above) was added to each T-225 flask by pipetting directly into the medium, without contacting the growth surface, followed by gentle mixing. A control T-225 flask was transfected with 40 μg of pEGFP plasmid, for determination of transfection efficiency.

After incubating cultures at 37° C. in transfection medium for 24 hours, the transfection medium was replaced with α-MEM+10% FBS+penicillin/streptomycin.

C. Selection of Transfected Cells

Cells that had incorporated plasmid DNA were selected 48 hrs after transfection by replacing the medium with 40 ml per flask of selection medium (growth medium containing 100 μg/ml G-418). Fresh selection medium was provided 3 days, and again 5 days after selection was begun. After 7 days, selection medium was removed and the cells were fed with 40 ml of growth medium. The cultures were then grown for about 3 weeks (range 18 to 21 days), being re-fed with fresh growth medium every 2-3 days.

Approximately 3 weeks after selection was begun, when surviving cells began to form colonies, cells were harvested. Medium was removed from the flasks using an aspirating pipette and 20 ml of DPBS without $Ca^{2+}/Mg^{2+}$, at room temperature, was added to each flask. The culture surface was gently rinsed, the wash solution was removed by aspiration and the rinse step was repeated. Then 10 ml of prewarmed (37° C.) 0.25% Trypsin/EDTA was added to each flask, rinsed over the growth surface, and the flasks were incubated for 5-10 min. at room temperature. Cultures were monitored with a microscope to ensure complete detachment of cells. When detachment was complete, trypsin was inactivated by addition of 10 ml of growth medium per flask. The mixture was rinsed over the culture surface, mixed by pipetting 4-5 times with a 10 ml pipette, and the suspension was transferred into a sterile 50 ml conical centrifuge tube. Cells harvested from several flasks could be pooled in a single tube. If any clumps were present, they were allowed to settle and the suspension was removed to a fresh tube.

The cell suspensions were centrifuged at 800 rpm (200×g) for 8 min at room temperature. Supernatants were removed by aspiration. Cell pellets were loosened by tapping the tube, about 10 ml of DPBS without $Ca^{2+}/Mg^{2+}$ was added to each tube and cells were resuspended by gently pipetting 4-5 times with a 10 ml pipette to obtain a uniform suspension.

D. Expansion of Transfected Cells

Cell number was determined for the suspension of transformed, selected cells and the cells were plated in T-225 flasks at $2 \times 10^6$ cells per flask (providing approximately 30% seeding of viable cells). This culture is denoted M2P1 (passage #1). M2P1 cultures were fed with fresh medium every 2-3 days, and when cells reached 90-95% confluence (usually 4-7 days after passage), they were harvested and replated at $2 \times 10^6$ cells per flask to generate passage M2P2. When M2P2 cultures reached 90-95% confluence, they were harvested for cryopreservation (Example 3) or for further assay DRCs prepared in this fashion were positive (>95%) for CD29, CD90 and CD105, and negative (<5%) for CD31, CD34 and CD45.

Example 3: Cryopreservation

MASCs and DRCs were frozen for storage according to the following procedure. MASCs were typically frozen after passage M2, and DRCs were typically frozen after passage M2P2. Processing 4-5 flasks at a time, medium was aspirated from the culture flasks, 10 ml of 0.25% Trypsin/EDTA (at room temperature) was added to each flask, gently rinsed over the culture surface for no longer than 30 sec, and removed by aspirating. Then 10 ml of warmed (37° C.) 0.25% Trypsin/EDTA was added to each flask, rinsed over the growth surface, and the flasks were incubated for 5-10 min. at room temperature. Cultures were monitored by microscopic examination to ensure complete detachment of cells.

When detachment was complete, 10 ml of α-MEM growth medium was added to each flask, rinsed over the culture surface, and detached cells were mixed by pipetting 4-5 times with a 10 ml pipette. The cell suspension was transferred into a sterile 250 ml conical centrifuge tube, and any large clumps of cells were removed. Cells harvested from 15-20 flasks were pooled into one 250 ml tube.

The tube was subjected to centrifugation at 800 rpm (200×g) for 8 min at room temperature. The supernatant was removed by aspirating. The pellet was loosened by tapping the tube, and about 25 ml of DPBS (−/−) was added to each tube. Cells were resuspended by gently pipetting 4-5 times with a 10 ml pipette to obtain a uniform suspension. Any clumps in the suspension were removed by pipetting each sample through a sterile 70 μm sieve placed in the neck of a 50 ml tube.

Cell suspensions were pooled in a 250 ml centrifuge tube and any remaining clumps were removed. The final volume was adjusted to 200 ml with DPBS (−/−) and the sample was subjected to centrifugation at 800 rpm (200×g) for 8 min at room temperature. The supernatant was removed by aspiration. The cell pellet was loosened by tapping, 20 ml of DPBS (−/−) was added to the tube and cells were resuspended by mixing well and gently pipetting with a 10 ml pipette. The final volume was adjusted with DPBS (−/−) to give an estimated concentration of approximately $0.5$-$1.0 \times 10^6$ cells/ml, usually about 4-5 ml per T225 flask harvested, or about 200 ml for a 40-flask harvest.

A viable cell count was conducted on the suspension, which was then subjected to centrifugation at 800 rpm (200×g) for 8 minutes. The supernatant was aspirated, and the cell pellet was resuspended in cold Cryo Stor solution (BioLife Solutions, Bothell, Wash.) to a concentration of $12 \times 10^6$ cells/ml. One ml aliquots were dispensed into vials, which were sealed and placed at 4° C. in a Cryo Cooler. Vials were transferred into a CryoMed (Thermo Forma) freezer rack and frozen.

Example 4: Thawing and Recovery

Frozen cells (MASCs or DRCs) were stored in liquid nitrogen. When needed for experiments, they were quickthawed and cultured as follows. A tube of frozen cells was placed in a 37° C. bath until thawed. The thawed cell suspension (1 ml) was immediately placed into 10 ml of growth medium and gently resuspended. The suspension was centrifuged at 200×g, the supernatant was removed, and cells were resuspended in growth medium to an estimated concentration of $10^6$ cells/ml. Live cells were counted by Trypan Blue exclusion and cells were plated at a density of $2\times10^6$ cells per T225 flask. Cells were cultured at 37° C. in a $CO_2$ incubator for 3-4 days until cell growth resumed.

Example 5: Preparation of Primary Rat Brain Cells

Rat brain cortex cells were isolated from commercially available cortexes of E 18 rat embryos (BrainBits, Springfield, Ill.). Storage medium was carefully removed from the tube in which the cortex was supplied, and 2 ml of 0.25% (w/v) trypsin/1 mM EDTA (Invitrogen, Gibco) was added. The tube was placed into a 37° C. water bath for 5-7 minutes with occasional shaking. The trypsin was carefully removed and the tissue was washed briefly with α-MEM/10% FBS. DNase (MP Biomedicals, Solon, Ohio) in PBS was added to a final concentration of 0.25 mg/ml, the tube was vortexed for 30 sec and the contents pipetted 10 times in a 1 ml micropipette tip. The suspension was transferred into a fresh tube and centrifuged at 1,000 rpm (200×g) for 1 min. The pellet was then resuspended in NeuroBasal/B27 medium containing 0.5 mM GlutaMAX™ and a portion of the resuspended cells was removed for determination of cell number using a hemocytometer. This procedure usually results in a cell viability of 92-98%. Isolated cells were then plated into pre-warmed (37° C.) plates coated with either ECM or PDL, at density no greater than $1.5\times10^4$ cells/cm$^2$ (see examples below). Unless indicated otherwise, culture medium for rat cortical cells was NeuroBasal/B27 plus 0.5 mM GlutaMax. The cells were allowed to grow for the times specified in the examples below, without medium change.

Example 6: Preparation of Plates Coated with MASC-Deposited Extracellular Matrix (ECM)

MASCs were plated in 12-well plates at densities of $1\times10^5$ cells/well and $2\times10^5$ cells/well (2.5 and $5\times10^4$ cells/cm$^2$), and grown for 4 days at 37° C./5% $CO_2$ in complete medium (α-MEM/10% FBS/penicillin/streptomycin). Control wells contained medium, but no cells. Medium was then changed to serum-free α-MEM and culture was continued at 37° C./5% $CO_2$. After 2 days, medium was aspirated from the wells, and replaced with 1 ml of 0.5% (v/v) sterile Triton X-100 (Sigma-Aldrich, St Louis, Mo.). (Subsequent experiments showed that similar results can be obtained using 0.1% Triton.) After 30 min at room temperature (RT), the Triton solution was removed and replaced with 1 ml of 0.3% (w/w) aqueous $NH_4OH$ (Sigma-Aldrich, St Louis, Mo.), and incubation at room temperature was continued for 3-5 min. The $NH_4OH$ solution was removed, and the wells were washed twice with PBS, then filled with either PBS or NeuroBasal/B27 plus 0.5 mM GlutaMAX™ and stored at 4° C. until use.

FIG. 1 shows a micrograph of ECM deposited by two concentrations of MASCs.

Example 7: Growth of Rat Brain Cells on Plates Coated with ECM Produced by MASCs ECM-coated plates, prepared and stored as described in Example 6 above, were either warmed at 37° C. for 30 min (if stored with NeuroBasal/B27/GlutaMAX™ in the wells) or PBS was removed and replaced with NeuroBasal/B27/GlutaMAX™ (if the plates had been stored with PBS in the wells). Rat cortical cells, prepared as described in Example 5 above, were added to the warmed ECM-coated plates, at density of $1.5\times10^4$ cells/cm$^2$ in 1 ml per well of NeuroBasal/B27/GlutaMAX™ medium and cultured at 37° C./5% $CO_2$ for 9 days. Cortical cells were also added, at the same density, to pre-warmed control plates coated with poly-D-lysine (PDL) and cultured under the same conditions for the same amount of time. PDL-coated plates were prepared by adding a solution of 10 μg/ml poly-D-Lysine (PDL, Sigma-Aldrich, St Louis, Mo.) to wells and incubating for 1 hr at room temperature. The liquid was aspirated, wells dried, washed with PBS, filled with NeuroBasal/B27/GlutaMAX™ or PBS and wells were stored at 4° C. until use.

Figure 2:
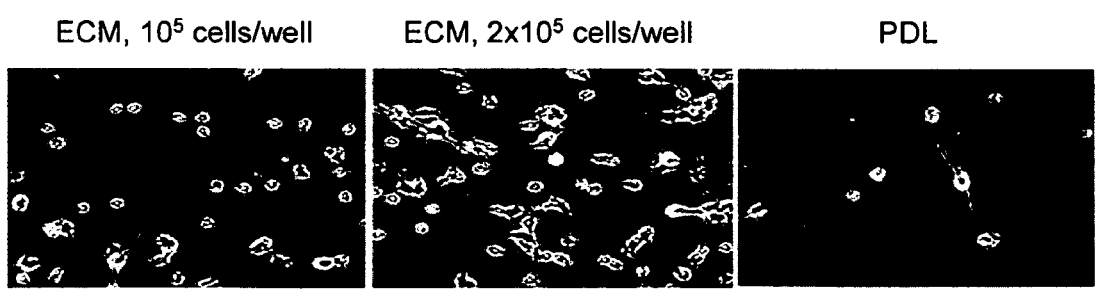
FIG. 2 shows micrographs (200×) of primary rat cortical neurons grown for 9 days on plates coated with MASC-deposited ECM (ECM, left-most and center panels) and poly-D-lysine (PDL, right-most panel). Growth on plates coated with ECM deposited by two different concentrations of MASCs is shown.

Neural cells attached to both MASC-ECM and PDL within an hour after plating. However, at later times (e.g., 16 hours after plating), it was observed that neurites grew more rapidly on ECM-coated plates and they tended to align with the fibrils present in the matrix. By contrast, on PDL, neurite outgrowth was slower and more randomly directed. By six days after plating, more cells, having denser neurite networks, were present on ECM than on PDL The appearance of rat cortical cells, grown in NeuroBasal/B27/GlutaMAX™ medium on plates coated with MASC-deposited ECM, was compared to that of rat cortical cells growth in the same medium on plates coated with PDL, and the results are shown in FIG. 2. After six days' growth on PDL-coated plates (right-most panel) few neurons, with moderate processes, were observed. On plates coated with MASC-deposited ECM, by contrast, numerous neurons, having extended processes, were observed (left-most and center panels). Accordingly, the extracellular matrix deposited by MASCs facilitates neuronal survival and growth.

Example 8: Neural Cells do not Bind to Components of the Medium

Fibronectin-coated wells were prepared by incubating wells with fibronectin at 5 μg/ml in PBS for 1 hour at room temperature. The solution was then aspirated and wells dried and washed once with PBS.

Coating of wells with laminin was achieved by incubating wells with laminin at 2 μg/ml in PBS for 2 hours at 37° C., and then washing 3 times with PBS.

Wells were coated with Matrigel® (BD Biosciences, Bedford, Mass.) according to the manufacturer's protocol.

To ensure that the cortical cells were attaching to the ECM, and not to components of the MASC growth medium that may have adsorbed to the wells during elaboration of the matrix, cell growth was tested in wells coated with growth medium, fibronectin and laminin. In these experiments, it was observed that, up to six days after plating, neural cells failed to grow in wells coated with FBS, fibronectin or laminin, by which time cells had attached and begun to extend neurites on plates coated with ECM or PDL. These results support the idea that the neural cells are attaching to the ECM, rather than to adsorbed components of the growth medium.

Growth of cortical cells on Matrigel®, a reconstituted basement membrane, was also assessed. Although cells were able to attach to surfaces coated with Matrigel®, they aggregated and formed neurospheres, leading to focal growth of the cells; in contrast to cells grown on ECM or PDL, in which the cells were more evenly distributed across the surface.

Example 9: Dose Response

A series of 96-well plates coated with MASC-deposited ECM was prepared essentially as described in Example 6, using different concentrations of MASCs, to determine whether the growth of brain cells was dependent on the number of MASCs used to deposit the ECM. Rat primary cortical cells were prepared as described in Example 5 and cultured on the coated plates as described in Example 7.

After either 5 or 13 days of culture on the coated plates, cell growth and survival was assayed by lysing the cells and measuring released intracellular lactate dehydrogenase (LDH), using a Roche LDH assay kit (Mannheim, Germany), as follows. Culture medium was removed from the well and 0.1 ml of 2% (v/v) Triton X-100 was added. A mixture of reagents A and B from the LDH kit was prepared according to the manufacturer's instructions, and 0.1 ml was added to each well. Approximately 20-30 min later, color was measured on a SpectraMax® Plus photometer (Molecular Devices, Sunnyvale, Calif.), reading at a wavelength of 490 nm, with a reference wavelength of 650 nm. Serial dilutions of frozen rat cortical cells, obtained as described in Example 5, above, were used to construct a standard curve. Alternatively, serial dilutions of purified bovine LDH were used as standards. The cells were thawed, lysed in Triton and serially diluted. Typically, color was allowed to develop until the standard sample containing the highest cell (or LDH) concentration provided a reading of approximately 1 OD unit. Measurements were analyzed using Soft Max Pro software (Molecular Devices, Sunnyvale, Calif.) and a standard curve was constructed by quadratic fit.

Figure 3:
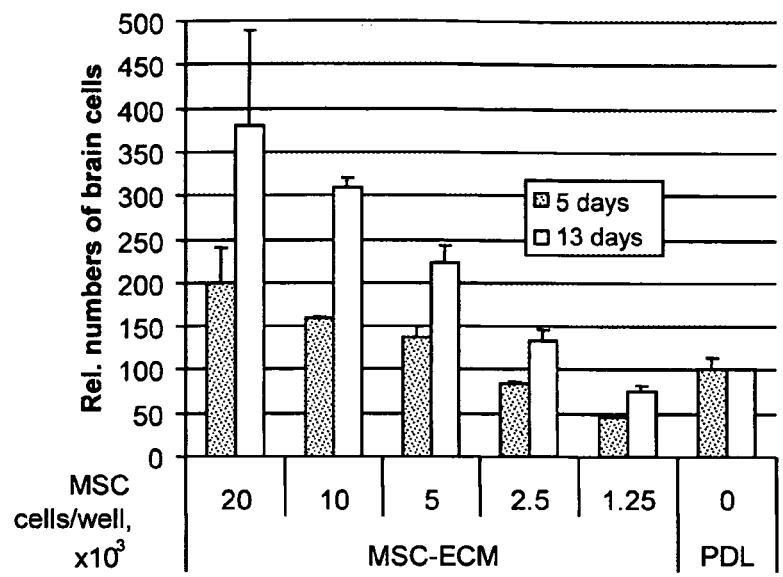
FIG. 3 shows relative cell number (determined from intracellular LDH levels) in cultures of primary brain cells grown for two different time periods (5 and 13 days) on plates coated with MASC-deposited ECM (MSC-ECM). Cell numbers are relative to the number of cells surviving, after growth for the same time periods, on plates coated with poly-D-lysine (PDL), which numbers were arbitrarily set to 100 for both culture periods.

The results, shown in FIG. 3, indicate that brain cell growth is positively correlated with the number of MASCs that were used to produce the ECM coating the well in which the cells were grown. When higher doses of MASCs were used, the number of cells present on ECM-coated plates significantly exceeded the number of cells present on PDL-coated plates. This effect became more pronounced with longer culture: for example, after 5 days of culture, the number of cells growing on plates coated with ECM elaborated by MASCS that were initially plated at a density of $2 \times 10^4$ cells/well was approximately twice the number growing on PDL-coated plates; while, after 13 days of culture, the ratio of surviving cells increased to almost four-fold.

Example 10: Growth of Rat Brain Cells on Plates Coated with ECM Produced by Differentiation-Restricted Descendents of MASCs MASCs can be subjected to treatments that alter their developmental capacity. See United States provisional patent application, filed even date herewith, inventor Irina Aizman, 61/005,211, client reference number SB7-PR1; see also Example 2 above. The ability of such "differentiation-restricted cells (DRCs)" to elaborate a matrix that supports and enhances survival of brain cells was tested and compared to that of the parent MASCs.

Figure 4:
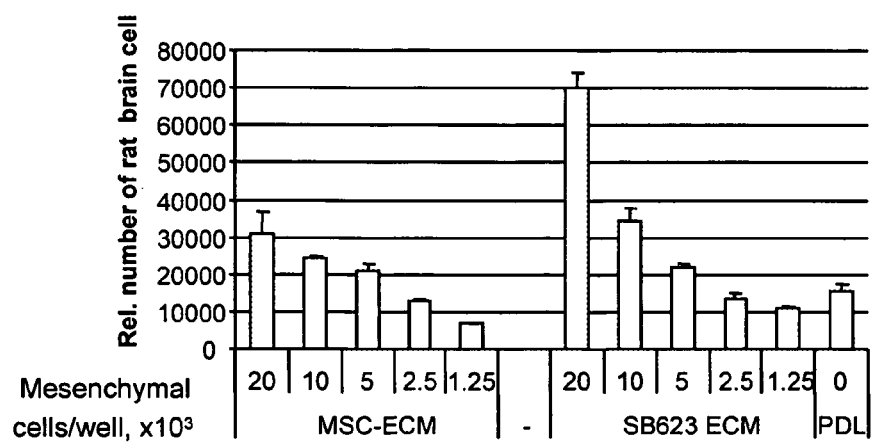
FIG. 4 shows relative cell number (determined from intracellular LDH levels) in cultures of primary brain cells grown for 13 days in wells coated with MASC-deposited ECM (MSC-ECM) and in wells coated with ECM deposited by DRCs (SB623 ECM). Different numbers of ECM-depositing cells were used in the preparation of the ECM-coated wells, as shown along the abscissa. Also shown is the relative cell number for primary brain cells grown under the same conditions in poly-D-lysine-coated wells (PDL).

MASCs and DRCs from the same donor were plated at several different concentrations (1.25, 2.5, 5, 10 and $20 \times 10^3$ cells per well; corresponding to 4, 8, 15, 30 and $60 \times 10^3$ cells/cm$^2$), then cultured (as described in Examples 7 and 9) for 6 days. At that point, cells were lysed with Triton (as described in Example 6), the cell lysates were removed from the wells and a portion of each lysate was used to determine relative cell numbers, based on released intracellular LDH. This measurement was used to confirm that the numbers of MASCs and/or DRCs per well was as expected, based on the initial number of cells plated. The wells were then treated with NH$_4$OH and washed as described in Example 6, and rat brain cortex cells (prepared as described in Example 5) were plated in the wells as described in Example 7. Cells were cultured, as described in Example 7, for 13 days. At 5 days and 13 days of culture, the relative cell number in each well was determined by LDH assay, as described in Example 9. The results, shown in FIG. 4, indicate that DRC-deposited ECM had an even greater supportive effect on neural cells than did MASC-deposited ECM. In particular, ECM elaborated by either MASCs or DRCs plated at or greater than a density of $1.5 \times 10^4$ cells/cm$^2$ (at which the cells were approximately 80% confluent at the time of ECM preparation) consistently supported better neural cell growth than did PDL; and ECM elaborated by DRCs plated at cell densities of $3 \times 10^4$ cells/cm$^2$ or greater supported more extensive cell growth that did that elaborated by MASCs plated at the same density.

Thus DRCs, in addition to having an altered differentiation capacity compared to their parent MASCs, also have a greater ability to elaborate a matrix conducive to the growth of neural cells. This could result from DRCs having an ability to produce more of the same type of matrix as that produced by MASCs, or may result from the ability of DRCs to elaborate a matrix that is qualitatively different from the matrix elaborated by MASCs.

Example 11: Test for Effects of ECM on Initial Adhesion of Cortical Cells

Since one of the functions of the extracellular matrix is to provide a surface to which cells adhere, it is possible that the beneficial effects of MASC- and DRC-deposited extracellular matrix on brain cell survival and growth is due to improved adhesion of the cells to the matrix and/or the culture surface. To test the effect of MASC-deposited ECM on cell adhesion, primary rat cortical cells, prepared as described in Example 5, were cultured in either MASC-deposited ECM-coated wells (prepared using different concentrations of MASCs, as in Example 8) or PDL-coated wells (prepared as described in Example 7). Two sets of wells (containing one PDL-coated well and a series of wells containing ECM from different numbers of MASCs) were analyzed: in one set, the cortical cells were grown in NeuroBasal/B27/GlutaMAX™ medium (as used in previous examples 7, 9 and 10); in the other set, the cortical cells were cultured in α-MEM. All determinations were carried out in duplicate.

Neural cells as described in Example 5 were plated at a density of $1.5 \times 10^4$ cells/cm$^2$ in 96-well plates, coated either with MASC ECM or with PDL. The cells were cultured for one hour (37° C., 5% CO$_2$); then the medium was removed and the wells were washed with PBS (containing Ca$^{2+}$ and Mg$^{2+}$). Cells remaining attached to the wells were lysed and analyzed for intracellular LDH as described in Example 9.

Figure 5:
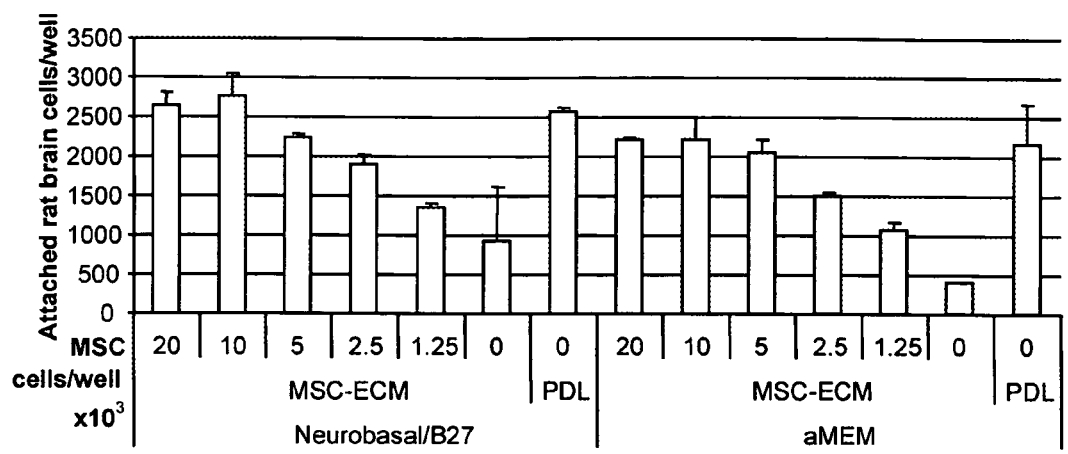
FIG. 5 shows relative numbers of rat primary cortical cells (determined by analysis of intracellular LDH levels) remaining attached to the culture surface after one hour of culture. Culture vessels were coated either with MASC-deposited ECM (MSC-ECM) or with poly-D-lysine (PDL). Different numbers of ECM-depositing cells were used in the preparation of the ECM-coated wells, as shown along the abscissa. Attachment assays were conducted using two different media for cell culture: either NeuroBasal/B27/GlutaMAX™. or α-MEM, as indicated.

The results are shown in FIG. 5. When cells were cultured for one hour and non-adherent cells were then washed off the culture surface, no difference in the number of cells adhering to PDL-coated wells and the number of cells adhering to wells coated with ECM deposited by higher doses of MASCs (the same doses that provided enhanced growth of the cells) was observed. Thus, the beneficial effects of ECM are not due to facilitation of initial adherence of the primary cortical cells, but become apparent only during later stages of culture. FIG. 5 also shows that there is no differences in adhesion whether the cortical cells are grown in a poor medium (α-MEM) or a rich medium (NeuroBasal/B27/GlutaMAX™).

Example 12: Enhancement of Brain Cell Growth in Poor Medium by ECM

Figure 6:
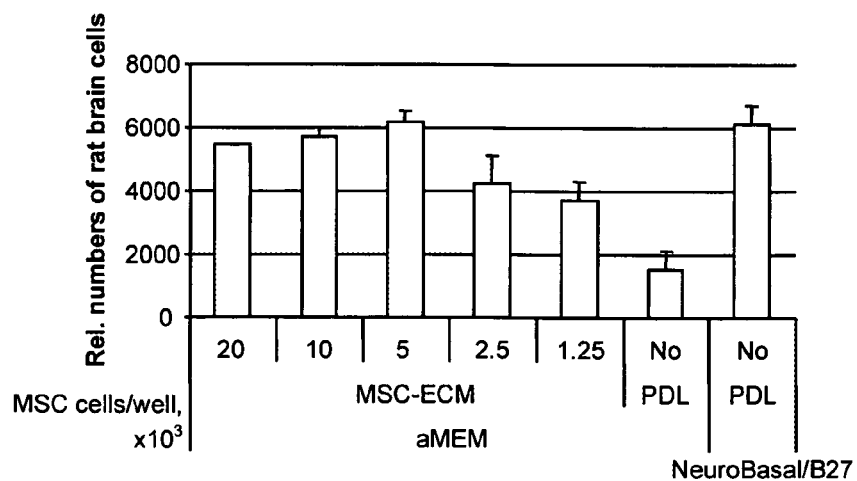
FIG. 6 shows relative cell number (determined from intracellular LDH levels) in cultures of primary brain cells grown in either NeuroBassal/B27 medium or α-MEM (as indicated). Cells were cultured for four days on plated coated with poly-D-lysine (PDL) or MASC-deposited extracellular matrix (MSC-ECM), as indicated. For the MSC-ECM-coated plates, the number of MASCs used in the preparation of the plates is indicated along the abscissa (No, 1.25, 2, 5, 5, 10, or 20×$10^6$ MASCs).

Rat primary cortical cells grew poorly in α-MEM, compared to their growth in NeuroBasal/B27/GlutaMAX™ medium. Four-day survival of neural cells grown on PDL-coated plates in α-MEM was approximately 25% of that in Neurobasal/B27/GlutaMAX™ medium on PDL-coated plates, as determined by intracellular LDH assay (FIG. 6, compare rightmost two bars). However, cortical cells grown in α-MEM on wells coated with ECM deposited by higher doses of MASCs survived as well, after four days' growth, as those grown in the richer Neurobasal/B27/GlutaMAX™ medium on PDL-coated plates (FIG. 6). Thus, the ECM can overcome the deficiency that led to poorer growth of rat cortical cells in α-MEM.

A similar effect was observed with ECM elaborated by DRCs.

Example 13: Expression of Neuronal Markers by Rat Cortical Cells Grown on ECM

The visual results shown above in FIG. 2, indicating enhanced neuronal growth when rat primary cortical cells were cultured on ECM, were confirmed by conducting immunohistochemical analyses for neuronal markers. For these experiments, rat cortical cells grown on poly-D-lysine, MASC-deposited ECM or DRC-deposited ECM were tested for the expression of the neuronal markers MAP2 and tau.

Rat primary cortical cells were grown on ECM- or PDL-coated plates for 3 days for the MAP2 assay, or for 13 days for the tau assay. At the conclusion of the growth period, cells were washed with PBS, fixed in 4% paraformaldehyde (Electron Microscopy Sciences, Fort Washington, Pa.) for 20 min, washed with PBS, and blocked with 0.3% Triton X-100, 5% normal donkey serum (NDS) (Jackson Immunoresearch Laboratories, West Grove, Pa.) for one hour. Primary antibodies to either MAP2 (monoclonal, Sigma-Aldrich, St Louis, Mo.) or tau (monoclonal, Chemicon, Temecula, Calif.) were used at dilutions of 1:1000 and 1:200, respectively. Isotype control was used as negative control for staining After incubation for 1-1.5 hr with the primary antibody, cells were washed and incubated with Cy3-conjugated AffiPure F(ab')$_2$ fragments of Donkey anti-Mouse IgG (minimal crossreaction) at 1:1000 (Jackson Immunoresearch Laboratories). After incubation for 1 hr with secondary antibody, wells or coverslips were washed with PBS and coverslips were mounted using ProLong Gold antifade reagent with DAPI (Invitrogen, Molecular Probes, Eugene, Oreg.). Cells were examined on either a Zeiss Axioskop or a Zeiss Axiovert 40CFL microscope, and photographs were taken with a Zeiss AxioCam MRm.

Figure 7:
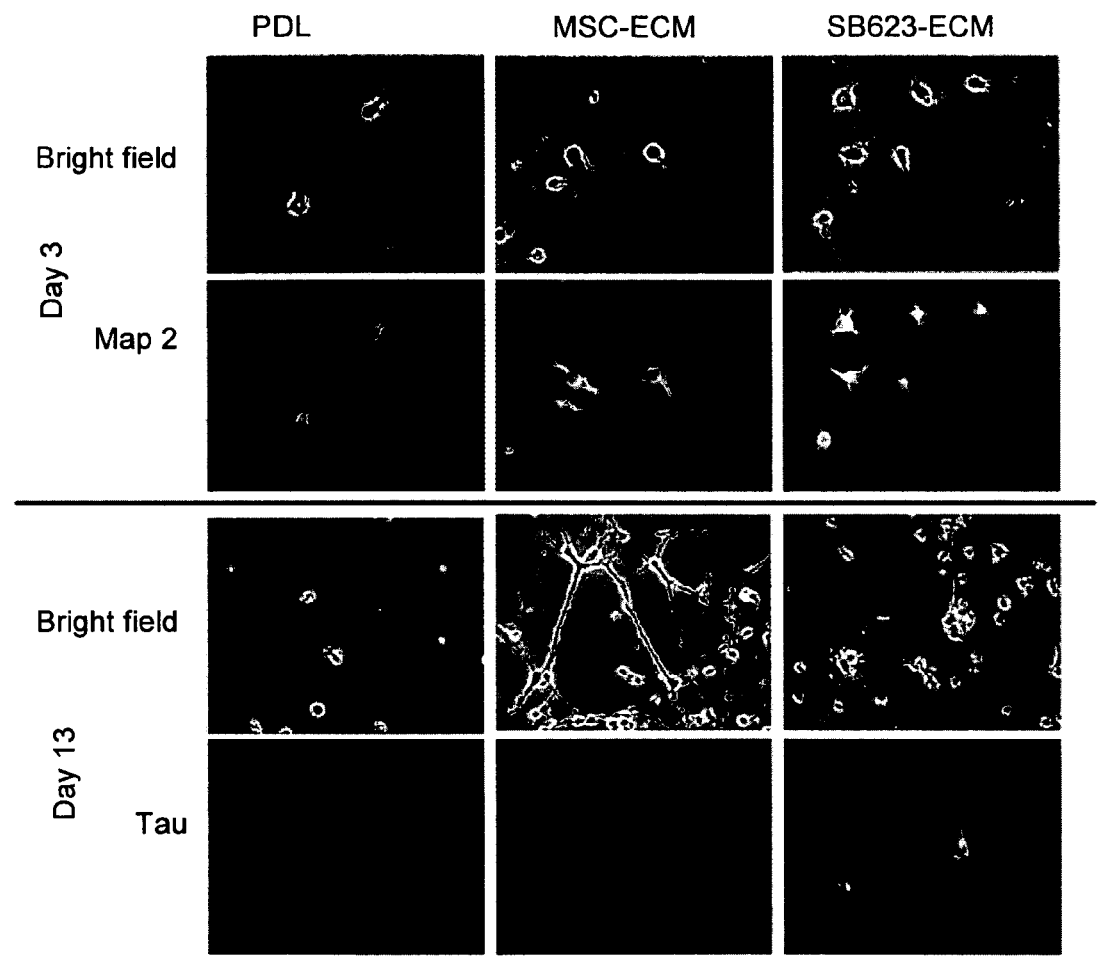
FIG. 7 is a collection of photomicrographs showing results of immunoassay for microtubule-associated protein-2 (MAP2) and tau protein in primary rat cortical cells grown on plates coated with poly-D-lysine (PDL), with MASC-deposited extracellular matrix (MSC-ECM) or with DRC-deposited extracellular matrix (SB623-ECM). Cells were assayed for MAP2 expression after 3 days of culture, separate cultures, grown under otherwise identical conditions, were assayed for tau expression after 13 days of culture. Fluorescence micrographs, and corresponding bright-field images, are shown. Magnification 400.times

The results, shown in FIG. 7, demonstrate that neurons growing on ECM (either MASC- or DRC-derived) possessed both a greater number of processes, and more fully-developed (i.e., longer) processes, than neurons growing on PDL. These cells also expressed significant levels of the neuronal markers MAP2 and Tau.

Example 14: Expression of Glial Markers by Rat Cortical Cells Grown on ECM

Figure 8:
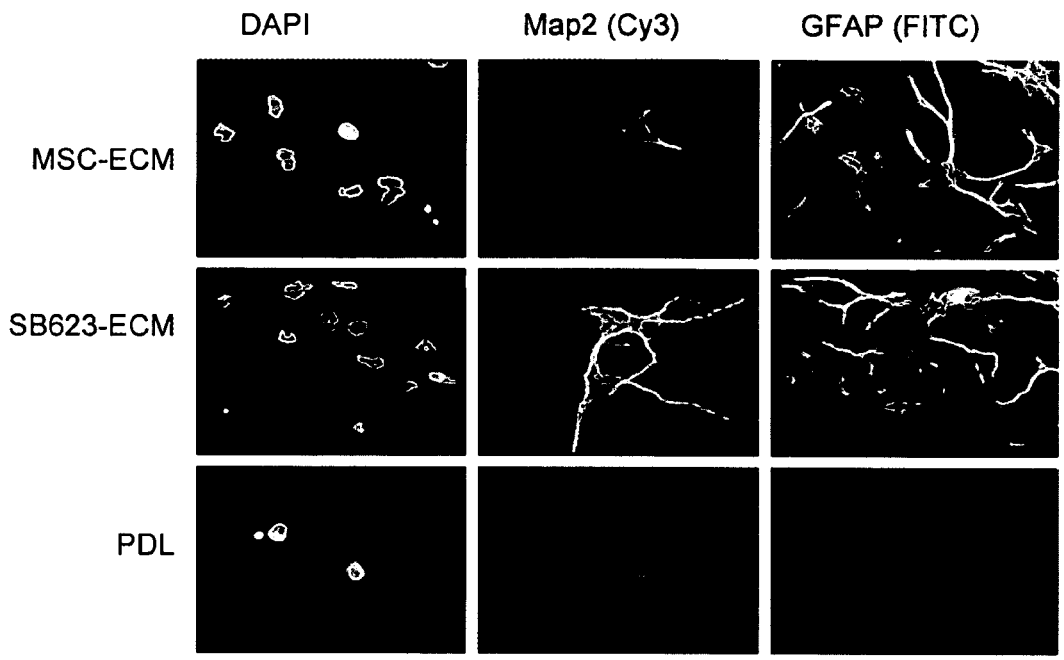
FIG. 8 is a collection of photomicrographs showing results of immunoassays for glial fibrillary acidic protein (GFAP) and microtubule-associated protein-2 (MAP2). Rat cortical cells were grown on plates coated with poly-D-lysine (PDL, bottom row), MASC-deposited ECM (MSC-ECM, top row) or DRC-deposited ECM (SB623-ECM, middle row), then stained with DAPI (left column), or reacted with anti-MAP2 (middle column, indicated by Cy3 fluorescence of conjugated secondary antibody) and anti-GFAP (right column, indicated by FITC fluorescence of conjugated secondary antibody). Magnification 1,000×
Figure 9:
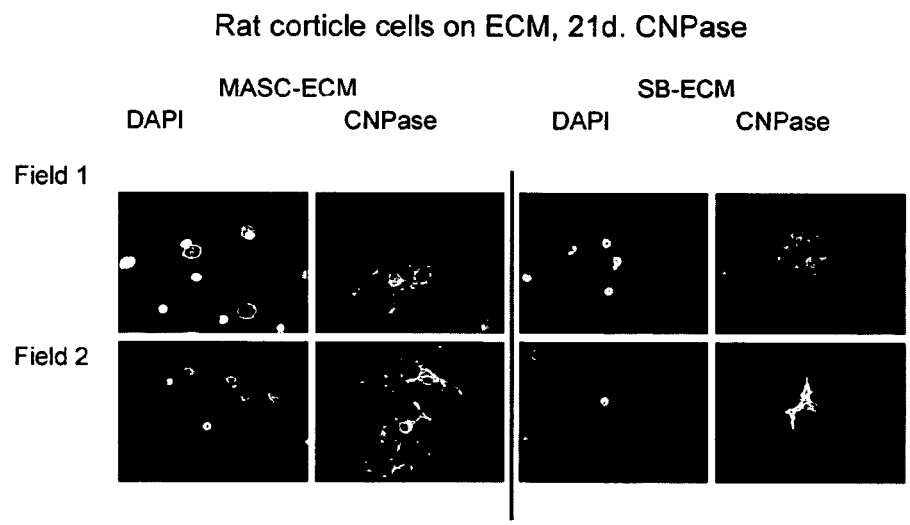
FIG. 9 is a collection of photomicrographs showing results of immunoassays for CNPase. Rat cortical cells were grown for 21 days on plates coated with either MASC-deposited ECM or DRC-deposited ECM, then stained with DAPI (first and third columns) and tested for reactivity with anti-CNPase (second and fourth columns). Two fields containing cells with CNPase immunoreactivity are shown. Magnification 1,000×

Rat primary cortical cells cultured on ECM were also tested for the expression of the astrocyte marker GFAP (glial fibrillary acidic protein, FIG. 8) and for the oligodendrocyte marker CNPase (FIG. 9). In testing for the expression of GFAP, the cultures were also tested for MAP2 reactivity, and were stained with DAPI to provide an estimate of cell number.

To test for GFAP and MAP2 expression, rat primary cortical cells were grown on ECM- or PDL-coated cover slips for 12 days. At the conclusion of the growth period, cells were fixed in 4% paraformaldehyde (Electron Microscopy Sciences, Fort Washington, Pa.) for 20 min and blocked with 0.3% Triton X-100, 5% normal donkey serum (NDS) (Jackson Immunoresearch Laboratories, West Grove, Pa.). Primary antibodies to either MAP2 (monoclonal, Sigma-Aldrich, St Louis, Mo.), or GFAP (rabbit polyclonal, DakoCytomation) were used at dilutions of 1:1000 and 1:1500, respectively. In some experiments, simultaneous assay for MAP2 and GFAP was conducted (i.e., MAP2 and GFAP antibodies were used in the same well). Isotype-matched antibody (for anti-MAP2) or normal rabbit serum IgG (for anti-GFAP) were used as negative controls for staining After incubation for 1 hr with the primary antibody, cells were washed and incubated with secondary antibodies. For MAP2, the secondary antibody was Cy3-conjugated AffiPure F(ab')$_2$ fragments of Donkey anti-Mouse IgG (minimal crossreaction) at 1:1000. For GFAP, the secondary antibody was FITC-conjugated AffiPure F(ab')$_2$ fragments of Donkey anti-Rabbit IgG (minimal crossreaction) at 1:4000 (both obtained from Jackson Immunoresearch Laboratories). After incubation for 1 hr with secondary antibody, wells or coverslips were washed with PBS and coverslips were mounted using ProLong Gold antifade reagent with DAPI (Invitrogen, Molecular Probes, Eugene, Oreg.). Cells were examined on either a Zeiss Axioskop or a Zeiss Axiovert 40CFL microscope, and photographs were taken with a Zeiss AxioCam MRm.

The results, shown in FIG. 8, confirmed that ECM supported the growth of more total cells (see nuclear staining by DAPI staining in left panels). In addition, cultures grown on ECM, but not on PDL, exhibited extensive GFAP staining, indicating the presence of large numbers of astrocytes (right panels). Among these astrocytes, MAP2-positive neurons were located in ECM cultures (center panels). By contrast, PDL supported only neuronal growth (i.e., MAP$^{2+}$ cells). Thus, ECM supported the growth of both neurons and astrocytes, and the neurons growing on ECM extended longer and more prominent neurites that did those growing on PDL.

CNPase (2',3'-cyclic nucleotide 3'-phosphodiesterase, or -phosphohydrolase) is a 47K protein found in myelin, that is expressed by oligodendrocytes and Schwann cells. To test for expression of CNPase, conditions were as described above for the GFAP assays, except that rat cells were grown for 21 days on ECM-coated plates, the primary antibody was an anti-CNPase monoclonal (Chemicon, Temecula, Calif.) used at 1:200 dilution, and the secondary antibody was Cy3-conjugated AffiPure F(ab')$_2$ fragments of Donkey anti-Mouse IgG (minimal crossreaction) at 1:1000 (Jackson Immunoresearch Laboratories). Results are shown in FIG. 9 and indicate that both MASC- and DRC-deposited ECMs supported the growth of oligodendrocytes. No cells showing immunoreactivity to CNPase were detected when rat neural cells were cultured on PDL-coated plates.

I claim:
1. An isolated extracellular matrix (ECM) produced by a method comprising:
   (a) culturing cells on a culture surface for a predetermined period of time; and

(b) removing the cells from the culture surface;
wherein the cells are obtained by a method comprising:
(i) transfecting marrow adherent stromal cells with a nucleic acid comprising sequences encoding a Notch intracellular domain;
(ii) culturing the cells of step (i) in the presence of a selective agent, thereby selecting cells comprising the nucleic acid; and
(iii) further culturing the selected cells in the absence of the selective agent;
further wherein the isolated ECM supports growth of neurons to a greater extent than an ECM produced by a marrow adherent stromal cell.

2. The isolated ECM of claim 1 wherein, in step (a), between $2.5 \times 10^4$ and $5 \times 10^4$ cells/cm$^2$ are plated for culture.

3. The isolated ECM of claim 1 wherein, in step (b), the cells are removed from the culture surface by sequential treatment with Triton X-100 and NH$_4$OH.

4. A method for stimulating the growth of neural cells, the method comprising culturing a population of neural cells on an isolated extracellular matrix (ECM) produced by a method comprising:
(a) culturing cells on a culture surface for a predetermined period of time; and
(b) removing the cells from the culture surface;
wherein the cells are obtained by a method comprising:
(i) transfecting marrow adherent stromal cells with a nucleic acid comprising sequences encoding a Notch intracellular domain;
(ii) culturing the cells of step (i) in the presence of a selective agent, thereby selecting cells comprising the nucleic acid; and
(iii) further culturing the selected cells in the absence of the selective agent.

5. The method of claim 4, wherein the neural cells are neurons.

6. The method of claim 4, wherein the neural cells are astrocytes.

7. The method of claim 4, wherein the neural cells are oligodendrocytes.

8. A method for treating neural degeneration or disorder in a subject, the method comprising transplanting to a site in the subject, an isolated extracellular matrix (ECM) produced by a method comprising:
(a) culturing cells on a culture surface for a predetermined period of time;
(b) removing the cells from the culture surface; and
(c) collecting the ECM from the culture surface;
wherein the cells are obtained by a method comprising:
(i) transfecting marrow adherent stromal cells with a nucleic acid comprising sequences encoding a Notch intracellular domain;
(ii) culturing the cells of step (i) in the presence of a selective agent, thereby selecting cells comprising the nucleic acid; and
(iii) further culturing the selected cells in the absence of the selective agent.

9. The method of claim 8, wherein the transplanting stimulates neurite outgrowth.

10. The method of claim 8, wherein the transplanting stimulates survival and growth of neurons.

11. The method of claim 8, wherein the transplanting stimulates growth and proliferation of glial cells.

12. The method of claim 8, wherein the ECM is transplanted in the central nervous system.

13. The method of claim 8, wherein the ECM is transplanted in the peripheral nervous system.

14. The method of claim 8, further comprising co-transplanting marrow adherent stromal cells to the site.

15. The method of claim 8, further comprising co-transplanting cells to the site; wherein the cells are obtained by a method comprising:
(i) transfecting marrow adherent stromal cells with a nucleic acid comprising sequences encoding a Notch intracellular domain;
(ii) selecting cells comprising the nucleic acid; and
(iii) further culturing the selected cells in the absence of selection.

* * * * *